United States Patent [19]
Reddy et al.

[11] Patent Number: 5,246,921
[45] Date of Patent: Sep. 21, 1993

[54] METHOD FOR TREATING LEUKEMIAS

[75] Inventors: Premkumar Reddy; Scott Shore, both of Philadelphia, Pa.

[73] Assignee: The Wistar Institute of Anatomy and Biology, Philadelphia, Pa.

[21] Appl. No.: 926,209

[22] Filed: Aug. 5, 1992

Related U.S. Application Data

[63] Continuation of Ser. No. 544,199, Jun. 26, 1990, abandoned.

[51] Int. Cl.$^5$ .............. A61A 31/70; C07H 17/00; C12P 21/06; C12N 15/00
[52] U.S. Cl. .............. 514/44; 536/23.2; 435/69.1; 435/172.3; 435/320.1
[58] Field of Search .............. 536/27, 23.2; 435/69.1, 435/172.3, 328.1; 514/44

[56] References Cited

U.S. PATENT DOCUMENTS

| | | | |
|---|---|---|---|
| 4,874,853 | 10/1989 | Rossi | 536/27 |
| 4,987,071 | 1/1991 | Cech et al. | 435/194 |
| 5,037,746 | 8/1991 | Cech et al. | 435/91 |
| 5,093,246 | 3/1992 | Cech et al. | 435/91 |
| 5,116,742 | 5/1992 | Cech et al. | 435/91 |

FOREIGN PATENT DOCUMENTS

| | | |
|---|---|---|
| WO8905852 | 6/1989 | PCT Int'l Appl. . |
| WO9104319 | 4/1991 | PCT Int'l Appl. . |
| WO9104324 | 4/1991 | PCT Int'l Appl. . |
| WO9118012 | 11/1991 | PCT Int'l Appl. . |
| WO9118625 | 12/1991 | PCT Int'l Appl. . |
| WO9118913 | 12/1991 | PCT Int'l Appl. . |
| WO9200080 | 1/1992 | PCT Int'l Appl. . |

OTHER PUBLICATIONS

N. Sarver et al, *Science*, 247:1222–1225 (1990).
J. Haseloff et al, *Nature*, 334:585–591 (1988).
D. E. Ruffner et al, *Gene*, 82:31–41 (1989).
M. Koizumi et al. *FEBS Letters*, 239(2):285–288 (1988).

*Primary Examiner*—John W. Rollins
*Attorney, Agent, or Firm*—Howson and Howson

[57] ABSTRACT

A novel ribozyme, capable of selectively cleaving the bcr-abl mRNA of a cell containing the Philadelphia Chromosome, thereby blocking synthesis of BCR-ABL protein is provided. Methods for using the ribozyme for treating leukemia patients and methods of producing the ribozymes are also provided.

16 Claims, 3 Drawing Sheets

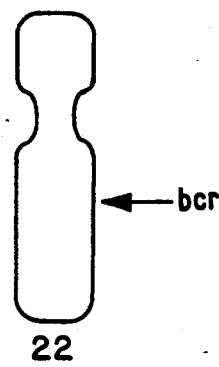
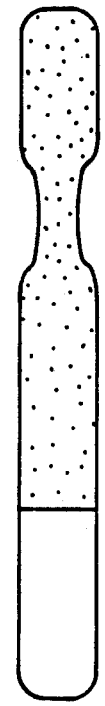
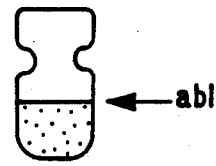
PHILADELPHIA CHROMOSOME
*FIG.1A*  *FIG.1B*
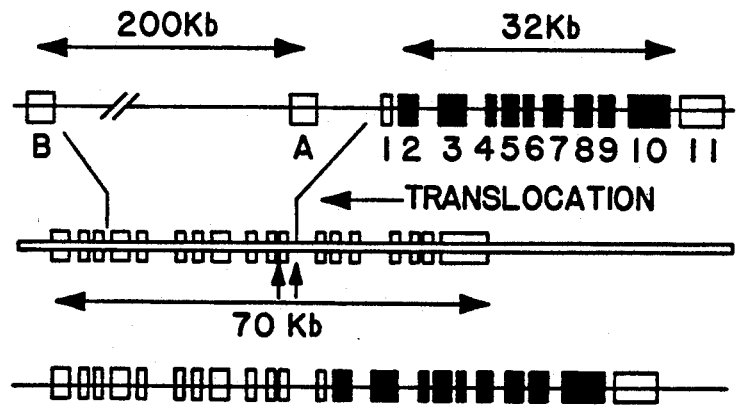
*FIG.1C*
*FIG.1D*
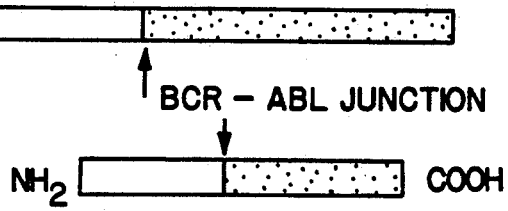
*FIG.1E*

METHOD FOR TREATING LEUKEMIAS

This application is a continuation of U.S. patent application Ser. No. 07/544,199, filed Jun. 26, 1990, now abandoned.

This invention refers generally to the treatment of cancers, and more specifically to methods for treating leukemias characterized by the presence of a chimeric protein such as those produced by a genetic translocation.

BACKGROUND OF THE INVENTION

Philadelphia chromosome is a hybrid chromosome resulting from a chromosomal translocation in which a small portion of the long arm of chromosome 9 is transferred to the long arm of chromosome 22. This chromosomal abnormality consistently associates with human chronic myelogenous leukemia (CML). CML is a disorder of hematopoietic cells which results in marked proliferation of granulocytic cells and often megakaryocytes.

Recent studies indicate that more than 95% of CML patients as well as 15-25% of ALL (Acute Lymphocytic Leukemia) patients harbor Philadelphia Chromosome which is designated as Ph+. Molecular studies by several groups demonstrate that during the formation of Philadelphia Chromosome, a portion of the c-abl gene is translocated from chromosome 9q34 to chromosome 22q11. Significantly, this translocation disrupts two genes, c-abl of chromosome 9 and the bcr gene of chromosome 22, resulting in the generation of a new, fused gene comprising portions of bcr and c-abl.

This chimeric gene, termed bcr-abl, produces a new protein, BCR-ABL which has several unique properties and appears to be the causative agent of the cancers with which it is associated (See FIGS. 1A through 1E). BCR-ABL protein is present only in tumor cells and its synthesis in these tumor cells is believed to be related to tumorigenicity.

Presently CML and ALL patients are treated chemotherapeutically with conventional therapeutics and radiation. Such treatment is plagued by well-known side-effects and is often of limited effect. No effective treatment for these leukemias is known. Thus, other compositions and methods for treating such cancers are being sought.

Certain naturally occurring RNA molecules, called ribozymes, possess the property of self-catalyzed cleavage. This reaction is shared by a number of small circular molecules which replicate in plants, either viroid RNAs, such as the avocado sunblotch viroid (ASBV) or satellite RNAs which are dependent on helper viruses, such as the satellite RNAs of tobacco ringpost virus and lucerne transient streak virus [Haseloff et al, *Nature*, 334:585-591 (1988)].

Comparison of several self-cleaving RNA sequences has led to the identification of a consensus secondary structure, termed "hammerhead", containing 11-13 conserved nucleotides at the junction of three helices that are precisely positioned with respect to the cleavage site. A hammerhead of less than 60 contiguous nucleotides was found to be sufficient for rapid cleavage in the absence of any protein [D. E. Ruffner et al, *Gene*, 82:31-41 (1989)]. Natural catalytic centers may be formed by contiguous regions in the RNA [P. Keese et al, in *Viroids and Viroid-Like Pathogens*, J. S. Semancik, ed. (CRC Press, Boca Raton, Fla., 1987), pp. 1-47; A. C. Forster et al, *Cell*. 49:211 (1987)] or by regions separated by a large number of nucleotides [C. J. Hutchines et al, *Nucleic Acids Res.*, 14: 3627 (1986); L. Epstein et al, *Cell*, 48: 535 (1987)]. Cleavage occurs 3' to the GUX triplet where X can be C, U, or A [O. C. Uhlenbeck, *Nature*, 328: 596 (1987); C. C. Sheldon et al, *Nucleic Acids Res.*, 17:5679 (1989)]. The essential constituents for the hammerhead can be on separate molecules, with one strand serving as a catalyst and the other as a substrate. Furthermore, RNA catalytic sequences require the conserved cleavage domain (GUX) to serve as the compatible substrates [Haseloff et al, supra].

One such hammerhead ribozyme, consisting of three stems or helices and a catalytic center containing 11-13 conserved nucleotides (5'-GAAAC(N)$_n$GUN(N)$_n$CUGA(N)GA-3'), has been employed to cleave HIV I gag transcripts [N. Sarver et al, *Science*, 247:1222-1225 (1990)].

There remains a need in the art for effective therapeutic compositions and methods to treat leukemia or ameliorate its effect on a human patient.

SUMMARY OF THE INVENTION

The present invention provides therapeutic compositions and methods for the treatment of leukemias, which are characterized by the presence of a chimeric protein which results from a chromosomal translocation.

In one aspect, the invention provides a composition comprising a synthetic RNA molecule, useful for the treatment of a leukemia characterized by the presence of a hybrid gene resulting from a chromosomal translocation coding for a protein which confers tumorigenicity to a human cell. The synthetic molecule comprises a single strand of ribonucleic acids comprising a sequence complementary to a sequence of the coding strand of the hybrid gene 5' to the breakpoint of the translocation and capable of hybridizing thereto, a second sequence complementary to a sequence of the coding strand of the hybrid gene 3' to the breakpoint of the translocation and capable of hybridizing thereto, and a sequence therebetween encoding a ribozyme capable of cleaving the hybrid gene at or near the breakpoint. The ribozyme sequence is preferably a hammerhead motif.

In another aspect the invention provides a composition comprising a synthetic RNA molecule, useful for the treatment of CML characterized by the presence of the hybrid gene bcr-abl coding for the BCR-ABL protein which confers tumorigenicity to a human cell. The synthetic RNA molecule comprises a single strand of ribonucleic acids comprising a sequence complementary to a sequence of the coding strand of the bcr-abl gene 5' to the breakpoint of the translocation and capable of hybridizing thereto, a second sequence complementary to a sequence of the coding strand of the hybrid gene 3' to the breakpoint of the translocation and capable of hybridizing thereto, and a sequence therebetween encoding a ribozyme capable of cleaving the hybrid chromosome at or near the breakpoint. These molecules may be synthesized by conventional means, or expressed from a recombinant expression vector.

A further aspect of the present invention provides recombinant vectors carrying the synthetic RNA molecules described above. Vectors of this invention are capable of expressing the RNA molecule and delivering the RNA molecule into a cell of a leukemic patient. These vectors are preferably recombinant retroviral vectors which have been altered to eliminate their pathogenicity. Other mammalian vectors may also be employed for this purpose which are capable of delivering the RNA molecule to the cell without otherwise damaging the cells.

Still another aspect of the present invention provides a method of treating leukemia with the above-described molecules and recombinant vectors. This method entails contacting cells of a patient suffering from leukemia with an effective amount of the synthetic RNA molecule. Once in the cell, the synthetic RNA molecule binds repeatedly to copies of the hybrid gene and the ribozyme cleaves the gene in a catalytic manner, rendering it incapable of coding for the chimeric protein.

Other aspects and advantages of the present invention are disclosed in the following detailed description.

BRIEF DESCRIPTION OF THE DRAWINGS

FIG. 1A illustrates chromosomes 9 and 22. FIG. 1B pictorially illustrates the formation of the Philadelphia chromosome from a translocation event between chromosomes 9 and 22. FIG. 1C schematically illustrates the c-abl gene on chromosome and the bcr gene of chromosome 22, and the location of the translocation. FIG. 1D schematically illustrates the chimeric chromosome where 3' bcr sequences have been replaced by c-abl sequences. FIG. 1E pictorially illustrates the Philadelphia chromosome, consisting of an approximately 8 Kb bcr-abl fused mRNA, which results in the expression of an approximately 210 Kd hybrid bcr-abl protein.

DETAILED DESCRIPTION OF THE INVENTION

Figure 2:
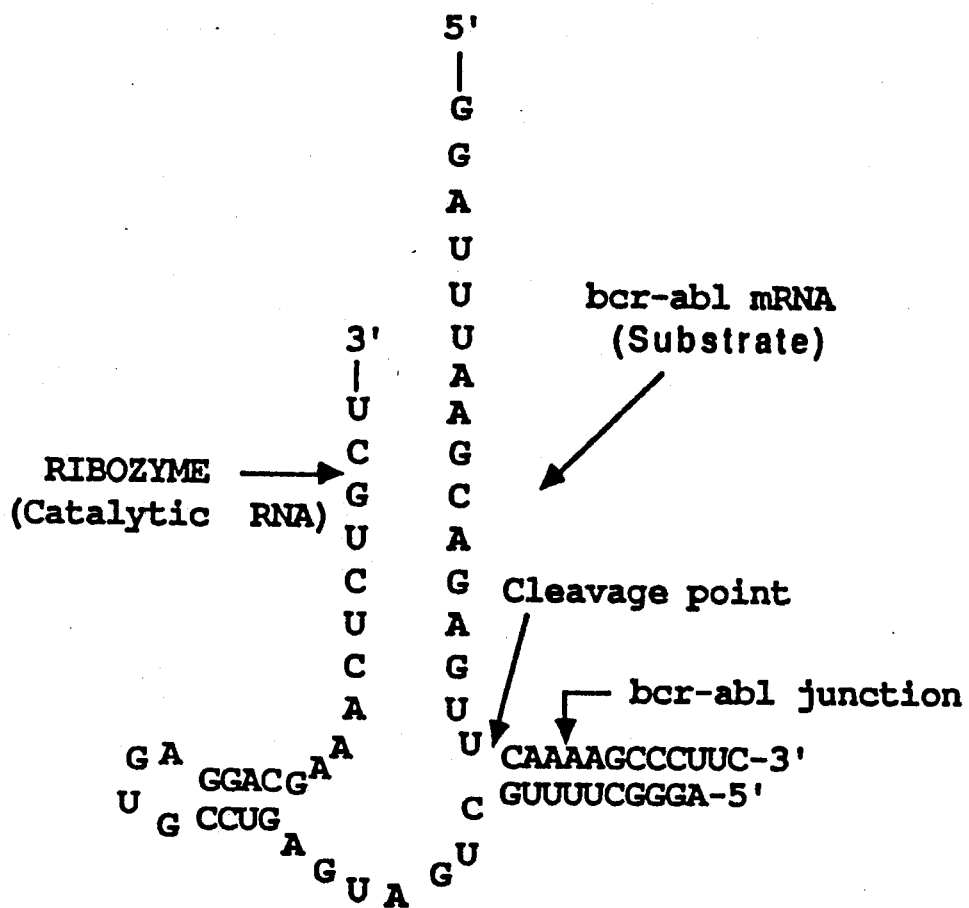
FIG. 2 illustrates the structure and sequence of one such synthetic ribozyme RNA molecule of this invention and the bcr-abl RNA substrate or "hammerhead" molecule. As is shown in FIG. 2, this RNA molecule is capable of forming duplexes with bcr-abl RNA.

The compositions and methods of the present invention are designed for the treatment of any leukemia or other cancer which is characterized by the presence of a tumorigenic chimeric protein such as that resulting from a chromosomal translocation, the gene encoding the protein having a ribozyme cleavage site at or near the chromosomal breakpoint. Exemplary disorders characterized by such a protein include chronic myelogenous leukemia, acute lymphocytic leukemia, as well as other leukemias, such as those involving c-myc 8q24 and bcl-1 and bcl-2.

The invention provides a synthetic RNA molecule or ribozyme. For purposes of simplicity, the following description relates to a novel RNA molecule of this invention designed for the cleavage of the bcr-abl mRNA produced by the Philadelphia chromosome. However, as noted above, the present invention is not limited to this molecule, but encompasses other molecules designed according to this invention for cleavage of similar genes in other cancers. The novel ribozyme has been designed to cleave the selected target chimeric gene after the ribonucleic acid sequence G-U-X, wherein X is the ribonucleotides A, U or C.

To use ribozyme-based reactions as a potential therapy for human leukemias, a hammerhead ribozyme motif that can cleave specifically the bcr-abl RNA thereby blocking the synthesis of BCR-ABL protein, the primary cause of these leukemias, is provided by this invention. The design of the hammerhead is such that it can only affect the oncogenic bcr-abl gene product without having any effect on normal bcr and c-abl gene transcripts. By cleaving the bcr-abl gene transcript, this ribozyme can prohibit synthesis of the BCR-ABL protein associated with tumor cells and, return the cells to normalcy.

The hammerhead ribozyme, which is preferred in this invention, comprises separate sequences: a catalytic sequence and a substrate binding sequence in two parts (the bcr-abl mRNA is the substrate). The ribozyme is a synthetic, catalytic RNA of between 35-45 nucleotides in length. A presently preferred ribozyme is about 40 nucleotides in length. The designed ribozyme may vary in structure so long as it contains the catalytic sequence. However, the cleavage rates of the ribozyme will vary depending upon the secondary (and possibly tertiary) structures of the hammerhead.

The hammerhead ribozyme of this invention comprises a single strand of ribonucleic acids comprising:

(1) a sequence complementary to a sequence of the coding strand of the hybrid gene 5' to the breakpoint of the translocation and capable of hybridizing to that part of the gene (a first substrate binding sequence);

(2) a second sequence complementary to a sequence of the coding strand of the hybrid gene 3' to the breakpoint of the translocation and capable of hybridizing thereto (a second substrate binding sequence), and (3) a sequence therebetween encoding a catalytic ribozyme domain capable of cleaving the hybrid chromosome at or near the breakpoint (the catalytic or ribozyme sequence).

Substrate binding sequences (1) and (2) above depend for their structure on the sequence of the hybrid gene which is targeted for destruction by the invention. These sequences are complementary to appropriate parts of the hybrid gene which flank the translocation breakpoint, e.g., the portion of the gene at which the two chromosomes are fused. The function of these sequences of the RNA molecule of this invention is to specifically isolate the hybrid gene RNA and position the ribozyme (3) for cleavage of the gene.

These sequences (1) and (2) are desirably between 5 to 11 nucleotides in length. More preferably, these flanking sequences are between 6 and 10 nucleotides in length. The length of these sequences provides a hybridization event with the target gene sufficient to permit cleavage of the gene at or near the breakpoint, thereby disabling the production of the hybrid tumorigenic protein. After the gene is cleaved, the RNA molecule is designed to dissociate from the pieces. The ability to release the fragments of the cleaved gene relates also to the length of the flanking sequences of the RNA molecule. The same RNA molecule may then encounter another gene and perform the same cleavage function repeatedly until the molecule is eventually degraded by the cell.

In a specific embodiment, a ribozyme molecule of this invention has a 40 nucleotide base sequence comprising

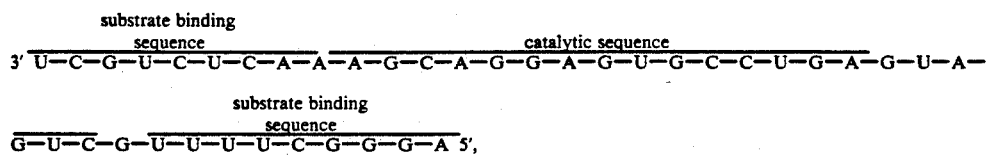

wherein U is Uridine, C is Cytosine, G is Guanidine, and A is Adenine. Optionally, the ribozyme may be provided with a cap structure, e.g. a 5'GpppG, which acts as a stabilizer in an intracellular environment.

The sequence of the RNA oncogene bcr-abl, i.e., the site on the bcr-abl gene transcript where the RNA molecule of this invention will bind is: 5' A-G-C-A-G-A-G-U-U (cleavage site)-C-A-A-A-A-G-C-C-C-U 3'. The ribozyme is designed so that cleavage occurs after the 5' GUU 3' sequence of the bcr-abl mRNA. FIG. 2 illustrates the binding of the ribozyme to the substrate (the bcr-abl gene transcript).

The ribozyme of this invention can be prepared by chemical synthesis or produced in recombinant vectors by conventional means [see, T. Maniatis et al, *Molecular Cloning (A Laboratory Manual)*, Cold Spring Harbor Laboratory (1982)].

As is described in exemplary form below, ribozyme RNA sequences may be synthesized conventionally by means of, for example, the RNA polymerase system such as T7 or SP6. bcr-abl mRNA substrates may be cloned from, for example, K562 cell line (available from the American Type Culture Collection, Rockville, Md., U.S.A., Accession Number ATCC# CCL 243) or BV173, EM2, Nalm-1, EM3, and any CML cell lines. The sequence of the bcr-abl gene is published in E. Shtivelman et al, *Nature*, 315:550–553 (1985). The RNAs are separated by electrophoresis and purified in acrylamide-urea gels.

The mechanism by which the ribozyme works is as follows: the substrate strand is designed in such a way that one half of it hybridizes to the bcr sequence of the hybrid gene and the other half of the substrate RNA binds to the abl sequence of the hybrid gene. The catalytic sequence is thereby placed in proximity to the 5'GUU3'sequence of the site of the targeted hybrid gene. Upon cleavage the bcr-abl gene transcript is destroyed, and the ability of the gene to direct the synthesis of BCR-ABL protein is interrupted. In the absence of the oncogenic protein, the cell returns essentially to normal.

Because the ribozyme effects only site-specific cleavage, normal cellular bcr and abl gene transcript sites therefore remain unaffected by the action of the ribozyme. Thus, only cells containing the translocation resulting in the Philadelphia Chromosome are altered by this ribozyme.

Desirably for both production of the ribozyme of this invention and to provide delivery systems for exposing bone marrow cells to the ribozyme, recombinant vectors are employed. The ribozyme construct may be placed in a viral vector, of which many are known to the art. Viral vectors are preferred because they have the capacity to infect the cell where the ribozyme must be located to function appropriately. Presently preferred vectors are retroviral vectors, adenoviral vectors, vaccinia vectors, and others, such as described by E. Gilboa, *Adv. Exp. Med. Biol.*, 241:29 (1988) and P. H. Pouwels et al, "Vectors for Animal Cells", in *Cloning Vectors: A Laboratory Manual*, ch.7 (Elsevier, Amsterdam: 1985). Other conventionally employed vectors designed for use in mammalian, bacterial, yeast, fungal or insect systems may be employed to recombinantly express the ribozyme of this invention, but are not preferred for delivery purposes into the cells.

The resulting viral vector is then exposed to the cells wherein the cells become infected, the ribozyme is replicated and functions as described above.

Alternative delivery systems for the ribozyme may employ other known components, such as a lipid delivery system, first described in P. L. Felgner et al, *Proc. Natl. Acad. Sci. U.S.A.*, 84:7413–7417 (1987). The lipid functions to fuse with the cells allowing the ribozyme to enter the cells. Transferrinfection of K562 cells, recently shown to be an effective alternative to retroviral infection, may be successfully employed as a delivery system [Cotten et al, PNAS, 87:4033 (1990)]. Other delivery systems may include direct addition of the ribozyme to cells, which has been shown to be successful with antisense DNA oligomers [S. L. Luke et al, PNAS, 86:3474–3478 (1989)].

The ribozyme of the present invention may thus be employed as a therapeutic agent in the treatment of leukemias and other cancers such as those characterized by the presence of the Philadelphia Chromosome. The method according to this invention may also be used in the treatment of other diseases, such as any leukemia or solid tumor which results from and contains the fusion of at least two normal genes, resulting in the generation of an abnormal chimeric gene product, or otherwise characterized by the presence of other chimeric gene products resulting from chromosomal translocations or other fusion mechanisms, wherein the resulting gene has a 5'GUX3' sequence close to the breakpoint. Other ribozymes may be designed according to this method for use in analogous treatments for these other cancers.

Preferably this treatment is accomplished by contacting bone marrow cells extracted from a patient ex vivo with a sufficient number of ribozymes, or vectors carrying ribozymes, for a time sufficient to effect cleavage of the oncogene present in the cells. Alternatively, the method may employ contacting the cells in vivo, for example, by administration directly into the bone marrow of a leukemic patient of vectors carrying the RNA molecule of the invention. When either method is applied to the cells of CML patients, the RNA molecule of this invention causes the specific destruction of the bcr-abl mRNA, resulting in the loss of synthesis of the tumorigenic BCR-ABL protein.

Once transmitted into the cellular environment via a vector, the ribozyme is expected to survive within the cell for a short period of time. Since there is not necessarily only a one to one relationship between the ribozyme and the target oncogene, a single ribozyme is expected to bind and cleave a number of oncogenic transcripts before being degraded or destroyed by the natural enzymes in the cells and/or the natural functions of the immune system.

The patient may be treated with conventional chemotherapy or radiation to substantially destroy the remaining bone marrow cells carrying the bcr-abl oncogene, and the treated cells are then returned to the patient. The treated cells, when returned to the patient may then be stimulated by various known hematopoietic growth factors to repopulate the bone marrow with cells which do not carry the oncogenic transcript.

This method has the advantage over conventional cancer or leukemia treatments, such as bone marrow transplant, of avoiding complications caused by lack of compatibility and rejection because in the present method only the patient's own cells are involved. Further, it is expected that many of the side effects associated with conventional chemotherapy may be avoided because the treatment takes place essentially ex vivo. However, this method may also be used in connection with other treatments, such as radiation or chemotherapy.

Figure 3:
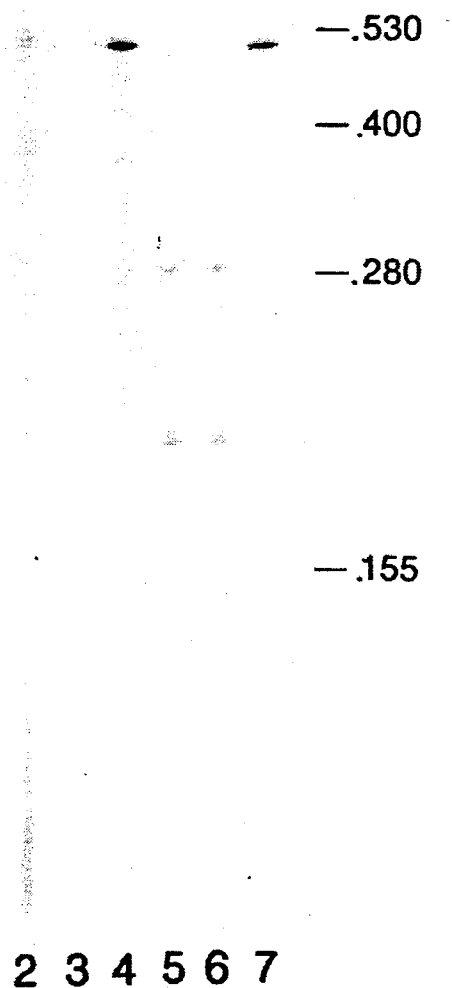
FIG. 3 illustrates an autoradiogram demonstrating the effects of the RNA molecule on the bcr-abl gene transcript. Lane 2 contains the $^{32}P$ labelled bcr-abl RNA transcript and $MgCl_2$ as a control; Lane 3 contains $MgCl_2$ and the unlabelled ribozyme as a control; Lane 4 contains EDTA and the labelled bcr-abl transcript as a control; Lanes 5 and 6 each contain $MgCl_2$, the ribozyme molecule and the labeled bcr-abl transcript; Lane 7 contains EDTA, the ribozyme molecule and the labeled bcr-abl transcript as a control. As seen in Lanes 5 and 6, when the bcr-abl RNA is exposed to the ribozyme molecule of this invention, the RNA is broken into two fragments of lower molecular weights, thereby rendering it inactive.

The in vitro reaction depicted in FIG. 3 indicates the applicability of the reaction to the in vivo conditions. The reaction was performed at 37° C. under physiological pH of 7.5 with the presence of the Mg++ cofactor. Under these conditions enzymatic activity will occur until the elimination of either the substrate or degradation of the ribozyme.

The number of ribozymes which are required can be determined in vitro by titration of a known substrate with known riboxyme until no activity is observed.

The following examples illustrate the compositions and methods of this invention.

Example 1 - Ribozyme RNA Synthesis

The ribozyme was synthesized as an oligonucleotide on an Applied Biosystems DNA synthesizer. The 40 mer ribozyme was purified by isolation from 20% polyacrylamide-7 M urea gels. The products are located by either autoradiography or UV shadowing. The resultant products band is crushed, and soaked for between 1 hour and overnight in 2 volumes of 0.5M NaOAc pH 7.0. The extracted RNA is concentrated by ethanol precipitation and resuspended in H$_2$O. Purified RNAs are stored in H$_2$O at −20° C.

The resulting ribozyme was 40 nucleotides in length with the following sequence:

```
         substrate binding
            sequence                         catalytic sequence
3' U—C—G—U—C—U—C—A—A—A—G—C—A—G—G—A—G—U—G—C—C—U—G—A—G—U—A— substrate binding
            sequence
  G—U—C—G—U—U—U—C—G—G—A 5',
``` wherein U is Uridine, C is Cytosine, G is Guanidine, and A is Adenine.

Example 2 - Preparing the bcr-abl Substrate

The 5' end of bcr-abl RNA containing the bcr-abl breakpoint was expressed by inserting a 420 bp fragment of bcr-abl cDNA, which was constructed from a library constructed from K562 mRNA, into the plasmid vector pGEM5 (Promega). This sequence is transcribed in vitro using T7 RNA polymerase in the presence of $^{32}$P-rCTP. The resulting labelled RNA was isolated and purified.

The vector containing the BCR-ABL fragment was linearized by NdeI digestion and transcribed in vitro using T7 RNA polymerase in the presence of =P-rCTP. The reaction was stopped after one hour at 37° C. by the addition of DNASE. Following digestion of the plasmid template, labelled RNA transcripts were loaded onto a 4% PAGE-7M urea gel and isolated by elution of the band from the gel slice. The purified RNA transcript was resuspended in H$_2$O and stored at −20° C. until use.

The T7 polymerase generated RNA transcript was 499 bases in length; with 73 bases of pGEM 5 polylinker sequence prior to the 420 bases of BCR/ABL substrate and 6 bases from the polylinker restriction linearization site. The GUU cleavage site is located 140 bases from the 5' end of the BCR/ABL specific sequences.

Analysis of the RNA transcript was used to characterize the cleavage products which would be expected if the assay described below in Example 3 proved the efficacy of the ribozyme. The 5' cleavage product should be 140+73=213 nucleotides and the 3' cleavage product should be 280+6=286 nucleotides. The intact transcript is 73+420+6=499 nucleotides. In the absence of cleavage, one specie is expected: an intact 499 nucleotide fragment extending from the T7 polymerase start site, to the end of the linearized plasmid. This includes the BCR/ABL segment as well as sequences from the pGEM5 expression plasmid. If cleavage of the bcr-abl RNA occurs, the 499 fragment is split into two fragments 213 and 286 nucleotides in length.

From this it was determined that the uncleaved bcr-abl gene transcript was 499 nucleotides in length. This RNA was used as a substrate in the test of Example 3 below.

Example 3 - Specificity of the Cleavage Site

To assess whether the synthetic ribozyme of Example 1 can cleave the bcr-abl mRNA substrate, the ribozyme of Example 1 and the RNA substrate of Example 2 (1 pmol of each) were mixed in a 10-μl reaction volume containing 50 mM Tris-HCl, pH 7.5. This resembles the physiologic pH of 7.4. As a control the MgCl$_2$ is omitted and 10 mM EDTA is added as the typical ribozyme-mediated cleavage is dependent on metal ions such as Mg++. The mixture is heated to 95° C. for 2 minutes and quick-cooled on ice. 10 mM MgCl$_2$ is added and then the mixture is incubated at 37° C. for 14 hours.

Following the incubation, the reaction products were analyzed on a 4% polyacrylamide gel under denaturing conditions. The results presented in FIG. 3 show that the synthetic hammerhead cleaves the substrate RNA containing the bcr-abl junction, in the expected manner.

After cleavage, the bcr-abl fragment sizes were 290 nucleotides and 160 nucleotides. [See lanes 5 and 6 in the gel of FIG. 3]. These results also show that the cleavage occurs very efficiently in the presence of Mg++ ions. In contrast, this cleavage reaction was inhibited by EDTA. These results indicate that the introduction of this synthetic RNA ribozyme into leukemic cells synthesizing bcr-abl gene transcripts will result in the specific degradation of bcr-abl RNA which, in turn, prevents the synthesis of the oncogene BCR-ABL. Thus, this treatment is expected to result in the reversal of the leukemic process.

Example 4 - Production and Use of a Vector for Delivery of the Ribozyme to Cells To deliver the ribozyme to a patient's leukemic cells, the ribozyme is inserted as a DNA fragment into a retroviral expression vector. A synthesized DNA fragment, such that its expression will result in the active ribozyme molecule, is cloned into a retroviral vector by standard methods (T. Maniatis et al, cited above). The retroviral vector, pC-1, contains the Moloney murine leukemia virus LTRs and a selectable neo gene. The crippled vector allows packaging and infection of the inserted gene. However, because the pathogenic portions of the parent virus have been removed, the pathogenicity of the parental viral infection has been eliminated. The recombinant virus containing the ribozyme DNA sequence is transfected into a packaging cell-line, such as PA3I17 or ψ2, to generate a producer cell line.

Bone marrow cells from a leukemic patient are infected either by co-cultivation with the producer cell-line or by incubation with cell-free virus containing supernatant. Following overnite infection, the bone marrow cells are washed in PBS and grow in vitro for a period of 14-21 days. Successfully infected cells are selected for by the inclusion of G418 (Gibco) in the medium at two days post-infection. The presence of the neo gene in the ribozyme-containing retrovirus allows for growth in the presence of this compound. Therefore cells which were not infected die. The population of infected bone marrow cells are transplanted into the patient. Bone marrow cells and/or peripheral blood samples are monitored by the PCR-RT technique using BCR-ABL specific primers to show the presence or absence of BCR/ABL transcripts and the success of the treatment.

Numerous modifications and variations of the methods of this invention are expected to occur to those of skill in the art. For example, the methods described above may be employed to design other ribozymes suitable for the treatment of other leukemias. Similarly, other recombinant techniques, vectors and methods for assembling the ribozymes may be selected by one of skill in the art without departing from this invention. Thus, the invention and such modifications are encompassed by the appended claims.

What is claimed is:

1. A synthetic RNA molecule useful for the treatment of a leukemia caused by the presence of a hybrid oncogene resulting from a chromosomal translocation, said RNA molecule comprising a single strand of ribonucleic acids comprising a sequence complementary to a sequence of the hybrid gene transcript 5' to the breakpoint of the translocation and capable of hybridizing thereto, a second sequence complementary to a sequence of the hybrid gene transcript 3' to the breakpoint of the translocation and capable of hybridizing thereto, and a sequence therebetween encoding a ribozyme capable of cleaving the hybrid gene transcript at or near the breakpoint, thereby blocking synthesis of the tumorigenic protein, said ribozyme comprising the nucleotide sequence: 3' A-A-G-C-A-G-G-A-G-U-G-C-C-U-G-A-G-U-A-G-U-C-5', wherein U is Uridine, C is Cytosine, G is Guanidine, and A is Adenine.

2. The RNA molecule according to claim 1 comprising the nucleotide sequence: 3' U-C-G-U-C-U-C-A-A-A-G-C-A-G-G-A-G-U-G-C-C-U-G-A-G-U-A-G-U-C-G-U-U-U-U-C-G-G-G-A-5', wherein U is Uridine, C is Cytosine, G is Guanidine, and A is Adenine.

3. The RNA molecule according to claim 1 wherein the oncogene is bcr-abl, and the protein is BCR-ABL.

4. A method for treating a patient having a leukemia characterized by the presence of a hybrid oncogene resulting from a chromosomal translocation comprising contacting cells of a patient suffering from leukemia with an amount of the RNA molecule of claim 1 sufficient for this RNA molecule to cleave the oncogene RNA transcript present in the cells, effectively blocking synthesis of a tumorigenic protein.

5. The method according to claim 4 wherein the cells are contacted with said molecule in vitro.

6. The method according to claim 4 wherein the cells are contacted with said molecule in vitro and subsequently re-introduced into the patient.

7. The method according to claim 4 wherein the cells are contacted with said molecule in vitro.

8. The method according to claim 4 wherein the leukemia is CML, ALL or contains an oncogenic gene product which is generated by the fusion of at least two genes.

9. The method according to claim 4 wherein the cells of the patient are contacted with said RNA molecule which is present in a recombinant vector.

10. A method for the treatment of disease associated with the expression of the Philadelphia Chromosome, comprising administration of the RNA molecule of claim 1.

11. The method according to claim 4 wherein the cells of the patient are contacted with said RNA molecule which is present in a lipid composition.

12. A recombinant vector comprising DNA which when expressed will yield the RNA molecule of claim 1.

13. The vector according to claim 12 capable of expressing the RNA molecule continually inside the cell.

14. The vector of claim 12 selected from the group consisting of a retroviral vector, an adenoviral vector, and a vaccinia vector.

15. A recombinant vector carrying the RNA molecule of claim 1 and capable of expressing the molecule in vitro.

16. The vector according to claim 15 comprising a vector selected from the group consisting of a mammalian vector, a bacterial vector, a yeast vector, a fungal vector, and an insect vector.

* * * * *

UNITED STATES PATENT AND TRADEMARK OFFICE
CERTIFICATE OF CORRECTION

PATENT NO. : 5,246,921
DATED : September 21, 1993
INVENTOR(S) : Premkumar Reddy and Scott Shore It is certified that error appears in the above-identified patent and that said Letters Patent is hereby corrected as shown below:

Col. 3, line 16, after "FIG. 1A" insert -- pictorially --;

Col. 8, line 1, delete "=P-rCTP" and insert thereof -- $^{32}$P-rCTP --;

Col. 9, line 21, delete "PA31I7" and insert thereof -- PA317 --.

Signed and Sealed this

Twelfth Day of April, 1994

Attest:

BRUCE LEHMAN

*Attesting Officer*    *Commissioner of Patents and Trademarks*